(12) United States Patent
Kumar et al.

(10) Patent No.: US 6,685,972 B2
(45) Date of Patent: Feb. 3, 2004

(54) **PROCESS FOR ISOLATING ARTEMISININ FROM *ARTEMISIA ANNUA***

(75) Inventors: Sushil Kumar, Lucknow (IN); Shiv Kumar Gupta, Lucknow (IN); Digvijay Singh, Lucknow (IN); Madan Mohan Gupta, Lucknow (IN); Dharam Chand Jain, Lucknow (IN); Atul Prakash Kahol, Lucknow (IN); Suman Preet Singh Khanuja, Lucknow (IN); Govind Ram, Lucknow (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 10/112,070

(22) Filed: Mar. 27, 2002

(65) Prior Publication Data

US 2003/0185914 A1 Oct. 2, 2003

(51) Int. Cl.$^7$ .................. A61K 35/78; A61K 31/335
(52) U.S. Cl. .................. 424/740; 424/774; 514/450; 514/452; 549/276; 549/348
(58) Field of Search .................. 424/740, 774; 514/450, 452; 549/276, 348

(56) References Cited

U.S. PATENT DOCUMENTS 5,413,928 A * 5/1995 Weathers et al.
5,955,084 A * 9/1999 Jain et al.
6,180,105 B1 * 1/2001 Wheatley et al.

FOREIGN PATENT DOCUMENTS

CN          1092073       * 9/1994

\* cited by examiner

*Primary Examiner*—Christopher R. Tate
(74) *Attorney, Agent, or Firm*—Sughrue Mion, PLLC

(57) ABSTRACT

The present invention relates to a process for the isolation of artemisinin, an antimalarial agent from the herb of the *Artemisia annua* plant, comprising of extracting the herb with ethanol, partitioning of the extract between water and hexane, followed by evaporative crystallization of artemisinin from hexane phase to produce substantially pure artemisinin.

18 Claims, No Drawings

PROCESS FOR ISOLATING ARTEMISININ FROM *ARTEMISIA ANNUA*

FIELD OF THE INVENTION

The present invention relates to a process for the isolation of artemisinin, an antimalarial agent from the herb of the *Artemisia annua* plant, comprising of extracting the herb with ethanol, partitioning of the extract between water and hexane, followed by evaporative crystallization of artemisinin from hexane phase to produce substantially pure artemisinin.

BACKGROUND AND PRIOR ART OF THE INVENTION

Artemisinin (Qinghaosu) is a sesquiterpene lactone endoperoxide having potent antimalarial activity (Klayman D L, 1985, Science 228, 1049). Clinical studies on artemisinin and its semisynthetic derivatives such as artemether, artesunate and arteether have been used in the treatment of malaria, including severe complicated-, multiple drug resistant- and cerebral-malaria. As being structurally different from commonly used antimalarials the problem of resistance and cross-resistance (that is now seriously limiting the effectiveness of such drugs) is not observed for artemisinin and its derivatives. Recently, methods have been reported for chemical synthesis of artemisinin but large scale economical synthesis is still not possible. Thus, plant *Artemisia annua* remains the sole source of artemisinin for the industry. The present invention provides a rapid, simple and economical method for the isolation of artemisinin from plant *Artemisia annua*.

Ancient methods (Klayman D L, Lin A J, Acton N, Scovill J P, Hoch J M, Milhous W K & Theoharides A D, 1984, Jour of Natural Products 47:715–717 and Rucker G, Mayer R & Manns D, 1986, Planta Medica, 3 : 245) involved the extraction of plant material with the petroleum ether followed by chromatographing the relatively crude extract on silica gel. The column was eluted with a mixture of 7.5% ethyl acetate in chloroform to obtain pure artemisinin. Later Singh A, Vishwakarma R A, Husain A, 1988, Planta Medica 64, 475–476 reported extraction of plant parts with n-hexane followed by chromatographing the extract on silica gel column. In this case elution was performed with the mixture of ethyl acetate and hexane. In these process major disadvantage was that the procedure depend upon chromatographing a relatively crude extract on silica gel. This needs large solute to adsorbent ratio 1:44, which is expensive.

Another method of artemisinin extraction involves the extraction of plant material with hexane, followed by partitioning the extract between hexane and acetonitrile followed by chromatographing the acetonitrile phase on silica gel (ElFerali F S, ElSohli H N, 1990, U.S. Pat. No. 4,952,603). Slow extraction of artemisinin in hexane needs hot percolation for longer duration, while for partitioning step, acetonitrile being relatively costly relatively costly solvent, increases cost of production for artemisinin. Another disadvantage of this method is that for obtaining artemisinin column chromatography is unavoidable. Yet another disadvantage is that artemisinic acid being predominant, it tends to elute with artemisinin, thus affecting the purity of artemisinin.

Jain D C, Tandon S, Bhakuni R S, Siddique M S, Kahol A P, Sharma R P, Kumar S, Bhattacharya A K, 1999, U.S. Pat. No. 5,955,084 suggests a process for simultenous production of artemisinin and essential oil from the plant *Artemisia annua*. In this process basic methodology for artemisinin extraction involves the extraction of plant material with hexane, followed by partitioning the extract between hexane and acetonitrile followed by chromatographing the acetonitrile phase on silica gel. Additionally the method suggests the extraction of essential oil from the residual marc by hydro-distillation and also describes a method for isolation of artemisinic acid and its conversion in to artemisinin. Overall the process disclosed is a complex amalgamation of several chemical reactions. However certain problems remained untouched such as the process being time consuming and costly affair because of using the hexane as extraction solvent, partitioning the extract between hexane and acetonitrile followed by chromatography.

A process for extracting aretannuin from *Artemisia annua* was reported by Zhang J, Fan D and Ma X (1994) Patent No. CN 1092073 A, which involve leaching the leaves of *Artemisia annua* with aqueous ethanol (<70% concentration) followed by extracting the leaching liquid with gasoline containing 30% of benzene or ethyl acetate in a continuous extracting device. Gasoline extract was then treated with activated carbon to decolorize followed by concentrating and crystallizing the artemisinin using ethanol. In this process large volumes of aqueous ethanol are needed to be fractionated with gasoline containing 30% benzene or ethyl acetate to make the ethanol clean for recycling. This lead to the transfer of most of the compounds extracted in ethanol:water mixture in to the gasoline and benzene mixture. Concentrating the gasoline mixture followed by crystallization of aretimisinin using ethanol results in crystallization. Use of commercial grade benzene during the processing is not suitable because of their possible toxic effects. The process used a mixture of solvents during transfer, which can not be re-used further.

Wheatley G W and Chapman T B, 2001, U.S. Pat. No. 6,180,105 disclosed another method for artemisinin production which involves extraction of the dry herb of *Artemisia annua* using liquid carbon dioxide and allowing the carbon dioxide to evaporate from the resultant mixture. This method is dependent on liquid carbon dioxide, which is obtainable only from liquid carbon dioxide preparing plant (a very costly device).

A reference may also be made to the Applicant's U.S. Pat. No. 5,995,084 which describes a process for the simultaneous production of artemisinin and essential oil from the plant *Artemisia annua*. In the aforesaid invention, artemisinic acid is separated from the artemisinin before it is treated with base.

Also, a reference may be made to the Applicants co-pending application Ser. No. 09/538,892 wherein an agricultural method for maximizing the artemisinin yield of the plant *Artemisia annua* is described. However, this application concentrates upon the agricultural method of scheduling the growing of the plant rather at the process for extraction of artemisinin.

The Applicant's The extraction with n-hexane petroleum ether are mostly used solvents, which take more time for extraction, and require hot percolation. These solvents are hazardous in nature. Subsequently most of the methods used chromatography to obtain artemisinin, which is a major cause for higher cost of production.

OBJECTS OF THE INVENTION

The main object of the present invention is to provide a simple, rapid, cost effective and practical method for the isolation of artemisinin from plant *Artemisia annua* without using chromatography, which yields artemisinin in substantial quantities and purity obviating the drawbacks of the prior art.

DETAILED DESCRIPTION OF THE PRESENT INVENTION

Accordingly, the present invention provides a process for the preparation of artemisinin from *Artemisia annua*, said process comprising:

(i) extracting plant parts of *Artemisia annua* with a non-aqueous polar solvent;

(ii) concentrating the extract of step (i) to recover the polar solvent;

(iii) adding water to the aforesaid concentrated extract;

(iv) adding hydrocarbon solvent to partition the aqueous extract of step(iii) into an aqueous layer and an organic layer;

(v) separating the organic layer from the solution of step (iv);

(vi) concentrating the organic layer of step (v) to obtain oily liquid;

(vii) adding ethyl acetate to the oily liquid of step (vi);

(viii) treating the solution of step (vii) with a conventional color absorbing substance to remove greenish pigmentation;

(ix) filtering the solution to remove the color absorbing substance, and (x) evaporating the solution followed by crystallization to obtain pure artemisinin.

In an embodiment of the present invention, wherein in step (i) dry leaves are taken for extraction.

In another embodiment of the present invention, the leaves are powdered before extraction.

In still another embodiment of the present invention, the non-aqueous polar solvent is selected from the group consisting of ethanol, methanol, acetone, methylisobutyl and hexane.

In yet another embodiment of the present invention, the non-aqueous solvent is ethanol.

In a further embodiment of the present invention, the ratio of the plant parts to the non-aqueous solvent is in the range of 1:5 to 1:10.

In one more embodiment of the present invention, the extraction of the plant parts is effected by percolating the herbs with ethanol for four to six hours.

In one another embodiment of the present invention, percolation of the herb is effected at temperatures between 20 to 50° C.

In an embodiment of the present invention, wherein in step (ii) the volume of the ethanolic extract is reduced to $\frac{1}{20}^{th}$ to $\frac{1}{100}^{th}$ of its original volume.

In another embodiment of the present invention, wherein in step (ii) the solvent recovered after concentration is reused in the process step (i).

In still another embodiment of the present invention, wherein in step (iii) water is added four times the quantity of the concentrated ethanolic extract.

In yet another embodiment of the present invention, wherein in step (iv) the hydrocarbon solvent used is selected from the group consisting of pentane, hexane and heptane.

In a further embodiment of the present invention, wherein in step (iv) the hydrocarbon solvent used is hexane.

In one more embodiment of the present invention, wherein in step (iv) the aqueous ethanolic extract is partioned in hexane in the ratio of 1:1 or 2:1.

In one another embodiment of the present invention, wherein in step (v) the organic layer is concentrated $\frac{1}{20}^{th}$ to $\frac{1}{100}^{th}$ of its original volume.

In an embodiment of the present invention, wherein in step (vii) 10–20% (v/v) ethyl acetate is added to the concentrated hexane solution to induce crystallization of artemisinin from the liquid.

In another embodiment of the present invention, the color-absorbing agent is selected from the group consisting of celite, activated charcoal and charcoal.

In still another embodiment of the present invention, wherein in step (x) artemisinin is obtained by slow evaporation followed by crystallization.

The process developed in the present invention provides an improved method of isolating the artemisinin from *Artemisia annua* plant populations. Our method involves cold extraction with ethanol/methanol, which on one hand allows complete extraction of artemisinin with rapidity and saves energy on the other hand in contrast to the methods of extraction using hexane or petroleum ether practiced routinely. Extraction in hexane or ether was very slow and needed hot percolation over several hours. Partitioning of the extract between water and hexane is economical and a completely non-obvious approach to enrich the extract with artemisinin, as 60–70% impurities of extract are left in water layer and complete transfer of artemisinin in to hexane layer. The hexane fraction thus obtained can be used for direct crystallization after a step of de-colorization for obtaining artemisinin without chromatography. Thus invention gives a new approach of isolating the artemisinin from its natural source *Artemisia annua* plant populations without using chromatography. The mild conditions used for extraction give a clean plant extract and avoid the possible degradation of artemisinin. As a consequence of this invention the process allows recovery of artemisinin per unit biomass at approximately half of the cost involved in the reported methods and is also suitable for small-scale industries too.

DETAILED DESCRIPTION OF THE PREFERRED EMBODIMENTS

In accordance with the method of the invention, dried pulverized leaves of *Artemisia annua*, may be extracted by continuous percolation over a period of four to six hours using five to ten fold volume of the non-aqueous solvent selected from ethanol or methanol. The said extraction process may be repeated three to five times using same solvent ratios to ensure maximum extraction of artemisinin from the herb. The resulting extract can be concentrated to 1 to 5% of the original volume by distillation under vacuum. The recovered solvent may be used again in the extraction process. The excess of water (four times of the reduced volume of ethanol extract) to be added to the concentrated to make it 80% aqueous followed by partitioning of the contents between water and hexane. For partitioning the aqueous content and hexane may be used in a ratio of 1:1 or 2:1 v/v. Partitioning of aqueous content with non-polar solvent may be repeated three to five times using the same solvent ratio in order to ensure maximum transfer of artemisinin to hexane fraction. The combined hexane fractions may be pooled together before they are distilled under vacuum (to recover the solvent for using again) to obtain 1–5% of its original volume. The concentrated liquid may be a light to dark green oily liquid. Ethyl acetate (10–20% v/v) is added to it. To remove the green pigmentation this liquid is treated with 1–3% w/v of any colour absorbing substance activated charcoal. The yellowish liquid obtained after removal of activete charcoal (by filtration) may be subjected to the evaporative crystallization yielding substantially pure artemisinin without using chromatography.

As an embodiment in the present invention the extraction of dry, pulverized leaves with non-aqueous ethanol may have several advantages over the previously used hexane or di-ethyl ether solvents. Besides extraction being rapid, ethanol will extract less amount of fatty material, which are considered as an obstacle in the purification and crystallization steps.

As an embodiment of the present invention the extract is partitioned between water and hexane in order to enrich the extract with respect to the artemsinin and remove as many impurities as possible from the concentrate to facilitate the crystallization of artemisinin.

According to another embodiment of the present invention, partitioning of the ethanol extract is carried out using water and hexane in a ratio ranging from (1:1 or 2:1), the process of partitioning can be repeated 3–5 times to ensure maximum transfer of artemisinin to hexane layer. The partitioning step results in a substantially exclusive transfer of the artemisinin into the hexane layer with concomitant reduction in the amount of material, i.e. only 30 to 35% weight of the original extract is transferred in to hexane layer.

According to yet another embodiment of the invention hexane fraction can directly be used for crystallization by slow evaporation after concentrating the hexane fraction and mixing 10–20% (v/v) of ethyl acetate.

In the prior art artemisinin is obtained through a hot extraction in hexane, petroleum ether, which takes more time for extraction. Hot extraction of plant leaves with the above solvent is hazardous and extract more colouring substances and fatty material, which are proved obstacle in purification. Whereas, the extraction with ethanol at room temperature is relatively rapid and obviates the co-extraction of colouring and fatty substances. Partitioning of the hexane extract between hexane and 20% aqueous acetonitrile results in transfer of artemisinin in to aqueous acetonitrile layer. Water is separated from aqueous acetonitrile layer by addition of sodium chloride to saturation prior to chromatography. For partitioning step acetonitrile being relatively costly raises the cost of production of artemisinin. Water and hexane combination, which has been used for liquid:liquid partitioning results in two distinct layers easily due to higher density differences. This will also be a preferable solvent system for partitioning of artemisinin on economic ground as compared to hexane and acetonitrile of the prior art. As a result of partitioning only 30 to 35% fraction of the extract remained in hexane thus enriching the extract in artemisinin. Wherefrom artemisinin could be directly crystallized using evaporative crystallization without going for chromatography, while it is not possible with acetonitrile layer, which consist of artemisinin after partitioning in methods described earlier.

The present invention further described with reference to the following examples which are given by way of illustration and therefore, should not be construed to limit the scope of the present invention in any manner.

EXAMPLE 1

Selection of Solvent for Extraction of Artemisinin

To select an efficient solvent for extraction of artemisinin different solvents systems were tested. For this 10 g of dry powdered leaves of *Artemisia annua* were extracted with methanol, 20% aqueous methanol, ethanol, 20% aqueous ethanol or hexane as a solvent individually in separate tubes. 10 ml of the solvent was taken out of the tube at 2, 4 and 6 h of incubation. The fraction was evaporated to dryness on a water bath, extract was solubilized in 2.0 ml solvent and spots (5 μl) were loaded on a TLC plate along with pure artemisinin dissolved in the respective solvent @ 1 mg/ml taken as controls. The TLC was carried out in a glass TLC tank saturated with the mobile phase hexane:diethyl ether (1:1), plates were developed to a height of 15 cm. Later plates were dried and spots were visualized by immersing the plates in a developing reagent (glacial acetic acid:sulfuric acid:anisaldehyde, 50:1:0.5), followed by heating the plate at 110° C. for 15 minutes or until pink spots of artemisinin appeared. For quantification, TLC spots corresponding to artemisinin were scanned at 540 and 610 nm dual wavelength mode of TLC scanner. The results obtained are presented in the form of % artemisinin extracted in to the solvent and are summarized in table-1. It is clear from the table that pure ethanol and methanol rapidly extract the artemisinin as compared to hexane, however after a certain period of time concentration of artemisinin starts diminishing in methanol and ethanol extracts in contrast to hexane extract possibly because of decomposition or transformation of artemisinin into another unknown compound. Mixing of water in methanol caused a severe decay of artemisinin extraction. Ethanol was more efficient for extracting more artemisinin in less time period as compared to methanol and hexane both. On the basis of lower cost and rapid extraction efficiency ethanol will be a suitable solvent.

TABLE 1

Extraction of *Artemisia annua* leaves with different solvents for different time periods. Artemisinin extracted is presented in the form of % fraction of total dry weight of herb.

| | % Artemisinin extracted in to the solvents | | | | |
|---|---|---|---|---|---|
| Extraction time (h) | Methanol | 20% aqueous methanol | Ethanol | 20% aqueous ethanol | Hexane |
| 2 | 0.44 | 0.20 | 0.50 | 0.33 | 0.30 |
| 4 | 0.50 | 0.005 | 0.58 | 0.41 | 0.35 |
| 6 | 0.50 | 0.005 | 0.59 | 0.45 | 0.56 |

EXAMPLE 2

Partitioning of Artemisinin

Pure artemisinin (0.2 g) was dissolved in different test tubes containing 1:1 (v/v) mixture of two non-miscible solvents, hexane and aqueous ethanol (i.e. ethanol mixed in water), where concentration of ethanol varied from 20 to 80%. After completely solubilizing the artemisinin in the mixture, two layers of hexane and ethanol were separated with the help of a separating funnel. The individual layer from different test tube was tested for the presence of artemisinin content by TLC as in example 1. The results showing the % fraction of artemisinin partitioned between the hexane and aqueous ethanolic layers separated from each tube are given in the Table-2.

TABLE 2

Data representing the trend of partitioning of artemisinin between hexane and ethanolic solution with water.

| Solvents used for partitioning (1:1 v/v) | % artemisinin in hexane layer | % artemisinin in ethanol layer |
|---|---|---|
| Hexane:20% aqueous-ethanol | 0 | 100 |
| Hexane:40% aqueous-ethanol | 10 | 90 |

TABLE 2-continued

Data representing the trend of partitioning of artemisinin between hexane and ethanolic solution with water.

| Solvents used for partitioning (1:1 v/v) | % artemisinin in hexane layer | % artemisinin in ethanol layer |
|---|---|---|
| Hexane:60% aqueous-ethanol | 70 | 30 |
| Hexane:80% aqueous-ethanol | 100 | 0 |

This example suggests that artemisisnin can be selectively transferred from ethatnolic extract of Artemisia annua in to hexane by maintaining the above ratios. From hexane fraction, artemisinin can be crystallized directly using known methods of evaporative crystallization.

EXAMPLE 3

Dry pulverized leaves of Artemisia annua (100 g) was extracted by continuous percolation over a period of four hours using 600 ml of ethanol at 30° C. temperature. The process of extraction was repeated four times using same solvent ratios. The combined extract was concentrated under vacuum to reduce the volume to 50 ml, volume was made up to 250 ml by adding water to it. The resulting mixture was partitioned with 250-ml hexane four times. The combined hexane layer was reduced under vacuum (to recover hexane) to 5% of its original volume to result in dark green oily liquid. A 20% v/v ethyl acetate was mixed to this liquid followed by treating this with 1% w/v activated charcoal. The liquid was filtered through a Whatman 3 mm filter paper to remove the activated charcoal. After filtration the resulting dark yellow liquid was subjected to evaporative crystallization. The resulting white, needle shaped crystals were separated out by vacuum filtration device and weighed. The total crystals yielded were 603 mg.

EXAMPLE 4

Dry pulverized leaves of Artemisia annua (100 g) was extracted by continuous percolation over a period of four hours using 1.0 litre of ethanol at 30° C. temperature. The process of extraction was repeated four times using same solvent ratios. The combined extract was concentrated under vacuum to reduce the volume to 80 ml, volume was made up to 400 ml by adding water to it. The resulting mixture was partitioned with 400-ml hexane four times. The combined hexane layer was reduced under vacuum to 50 ml volume to result in dark green oily liquid. A 20% v/v ethyl acetate was mixed to this liquid followed by treating this with 1% w/v activated charcoal. The liquid was filtered as in example 3 and subjected to evaporative crystallization. The artemisinin crystals obtained were weighed to be 605 mg.

EXAMPLE 5

Dried pulverized leaves of Artemisia annua (100 g) were extracted as in example 3. The concentrated extract 50 ml was made up to 250 ml by adding water to it. The resulting mixture was partitioned with 125 ml hexane five times. The combined hexane layer was reduced under vacuum to 50 ml dark green oily liquid. A 20% v/v ethyl acetate was mixed to this liquid followed by treating this with 1% w/v activated charcoal. The liquid was filtered through a whatman filter to remove the activated charcoal. After filtration the resulting dark yellow liquid was subjected to evaporative crystallization. The resulting white, needle shaped crystals were separated and weighed. The total artemisinin yield was 601 mg.

EXAMPLE 6

Extraction of Artemisia annua leaves was performed as described in example 3 but under varied temperatures 20, 30, 40 and 50° C. conditions in separate vials. The concentrated extracts 50 ml each obtained after was concentrating under vacuum were made to 250 ml by adding water to them separately. The resulting mixtures were partitioned with 250-ml hexane three times individualy. The hexane layers were reduced under vacuum to 5% of their original volumes, the dark green oily liquids. A 20% v/v ethyl acetate was mixed to each liquid followed by treating them with 1% w/v activated charcoal. The liquids were filtered and resulting dark yellow liquids were subjected to evaporative crystallization individualy in separate vials. The resulting artemisinin crystals were separated and weighed. The crystal yields were 410, 603, 600 and 550 mg at temperatures 20, 30, 40 and 50° C. respectively.

EXAMPLE 7

Dried pulverized leaves of Artemisia annua (1.0 kg) were extracted by continuous percolation over a period of four hours using 6 litres of ethanol at 30° C. temperature. The process of extraction was repeated four times using same solvent ratios. The combined extract was concentrated under vacuum to reduce the volume to 400 ml, volume was made up to 2.0 liters by adding water to it. The resulting mixture was partitioned with 2.0 liters hexane three times. The combined hexane layer was reduced under vacuum (to recover hexane for using again) to 300 ml dark green oily liquid. A 60 ml ethyl acetate was mixed to this liquid followed by treating this with 1% w/v activated charcoal (for removal of the green pigmentation). The resulting dark yellow liquid after filtration was subjected to evaporative crystallization. The artemisinin crystals were separated and weighed. A total of 5.95 g artemisinin crystals were obtained.

EXAMPLE 8

Dried pulverized leaves of Artemisia annua (100 g) were extracted by continuous percolation over a period of four hours using 600 ml of methanol at 30° C. temperature. The process of extraction was repeated four times using same solvent ratios. The combined extract was concentrated under vacuum to reduce the volume to 50 ml, volume was made up to 250 ml by adding water to it. The resulting mixture was partitioned with 250-ml hexane three times. The combined hexane layer was reduced 5% of its original volume to result in dark green oily liquid. A 20% v/v ethyl acetate was mixed to this liquid followed by treating this with 1% w/v activated charcoal. The liquid was filtered through a whatman filter to remove the activated charcoal. After filtration the resulting dark yellow liquid was subjected to evaporative crystallization. The resulting white, needle shaped crystals were separated out by vacuum filtration device and weighed. The artemisinin crystals obtained were 320 mg.

Advantages of the Process of the Present Invention:

The improved process of production of artemisinin, the subject matter of this patent offered a number of advantages such as 1. Extraction with ethanol is rapid and thus less time consuming.

2. Extraction is energy saver as heating is not required during the process.

3. Partitioning of extract between water and hexane to obtain artemisinin is a better option as compared to acetonitrile and hexane because of being economical.

4. The hexane layer obtained after partitioning can be used for crystallization of artemisinin without chromatography.

5. Overall process offers 30 to 40% reduction of production costs of artemisinin over prior art.

6. Any possible contamination of toxic chemicals in artemisinin due to using the commercial grade hexane during extraction may be avoided.

7. Setting up costly devise for liquefying the carbon dioxide is not required.

8. Since method does not need very large infra structure, the extraction of artemisinin can be easily planned in rural areas.

9. Overall process is efficient and economical as solvents used in the process are being recovered and reused.

We claim:

1. A process for the preparation of artemisinin from *Artemisia annua*, said process comprising:
   (i) extracting plant parts of *Artemisia annua* with a non-aqueous polar solvent;
   (ii) concentrating the extract of step (i) to recover the polar solvent;
   (iii) adding water to the aforesaid concentrated extract;
   (iv) adding hydrocarbon solvent to partition the aqueous extract of step (iii) into an aqueous layer and an organic layer;
   (v) separating the organic layer from the solution of step (iv);
   (vi) concentrating the organic layer of step (v) to obtain an oily liquid;
   (vii) adding ethyl acetate to the oily liquid of step (vi);
   (viii) treating the solution of step (vii) with a color absorbing agent to remove greenish pigmentation;
   (ix) filtering the solution to remove the color absorbing substance, and
   (x) evaporating the solution followed by crystallization to obtain pure artemisinin.

2. A process as claimed in claim 1, wherein in step (i) dry leaves are extracted with the non-aqueous polar solvent.

3. A process as claimed in claim 2, wherein the leaves are powdered before extraction.

4. A process as claimed in claim 1, wherein the non-aqueous polar solvent is selected from the group consisting of ethanol, methanol, acetone, methylisobutyl and hexane.

5. A process as claimed in claim 1, wherein the non-aqueous polar solvent is ethanol.

6. A process as claimed in claim 1, wherein the ratio of the plant parts to the non-aqueous polar solvent is in the range of 1:5 to 1:10.

7. A process as claimed in claim 1, wherein the extraction of the plant parts is effected by percolating plant parts with ethanol for four to six hours.

8. A process as claimed in claim 5, wherein extraction is carried out in the temperature range of 20 to 50° C.

9. A process as claimed in claim 1, wherein in step (ii) the volume of the non-aqueous polar solvent is reduced to $1/20^{th}$ to $1/100^{th}$ of its original volume.

10. A process as claimed in claim 1, wherein in step (ii) the non-aqueous polar solvent recovered after concentration is reused in the process step (i).

11. A process as claimed in claim 1, wherein step (iii) water is added four times the amount of the concentrated extract.

12. A process as claimed in claim 1, wherein step (iv) the hydrocarbon solvent used is selected from the group consisting of pentane, hexane and heptane.

13. A process as claimed in claim 1, wherein step (iv) the hydrocarbon solvent is hexane.

14. A process as claimed in claim 5, wherein step (iv) the aqueous extract is partioned in hexane in the ration of 1:1 or 2:1.

15. A process as claimed in claim 1, wherein step (v) the organic layer is concentrated $1/20^{th}$ to $1/100^{th}$ of its original volume.

16. A process as claimed in claim 1, wherein in step (vii) 10–20% (v/v) of the ethyl acetate is added to a solution containing a reduced amount of hexane in order to induce crystallization of artemisinin from the liquid.

17. A process as claimed in claim 1, wherein the color-absorbing agent is selected from the group consisting of celite, activated charcoal and charcoal.

18. A process as claimed in claim 1, wherein step (x) artemisinin is obtained by slow evaporation followed by crystallization.

* * * * *